United States Patent [19]

Vogl et al.

[11] Patent Number: 4,745,194
[45] Date of Patent: May 17, 1988

[54] ULTRAVIOLET LIGHT ABSORBERS HAVING TWO DIFFERENT CHROMOPHORS IN THE SAME MOLECULE

[75] Inventors: Otto Vogl; Shanjun Li, both of Brooklyn, N.Y.

[73] Assignee: The United States of America as represented by the United States Department of Energy, Washington, D.C.

[21] Appl. No.: 539,366

[22] Filed: Oct. 6, 1983

[51] Int. Cl.⁴ ............................................. C07D 249/20
[52] U.S. Cl. ...................... 548/261; 524/91; 548/260
[58] Field of Search ................................ 548/260, 261

[56] References Cited

U.S. PATENT DOCUMENTS 3,213,058 10/1965 Boyle et al. .......................... 548/261

FOREIGN PATENT DOCUMENTS 2835529 3/1979 Fed. Rep. of Germany ...... 548/261
9061070 6/1974 Japan ..................................... 546/26
1212466 11/1970 United Kingdom ................ 548/260

OTHER PUBLICATIONS

Balough et al., "Volatility . . . Polymer Mixes", Chem. Abst. 87: 185422b.
Volkotraub et al., "Spectroscopic Characteristics . . . 2-(2′-Hydroxyphenyl) Benzotriazole . . . " Chem. Abst. 84: 151415z.
Balough et al., "Volitability of Ingredients . . . of Polymer Mixtures," *Plasty Kawc,* 14 (7), 204–7.
Volkotraub et al., "Special Spectral Characteristics . . . of 2-(2′-Hydroxyphenyyl) Benzotriazole–Type Photostabilizers", Vysokomol. Soyed, A18:3, 553–6, (1976).

*Primary Examiner*—Donald G. Daus
*Assistant Examiner*—Mark Noel
*Attorney, Agent, or Firm*—Judson R. Hightower; Richard E. Constant

[57] ABSTRACT

Ultraviolet light absorbing compounds having two different chromophors in the same molecule, particularly the benzotriazole chromophor and either the dihydroxybenzophenone or dihydroxyacetophenone chromophor; specifically, the two compounds 3,5-[di(2H-benzotriazole-2-yl)]-2,4-dihydroxyacetophenone and 3,5-[di(2H-benzotriazole-2-yl)]2,4-dihydroxybenzophenone.

2 Claims, 3 Drawing Sheets

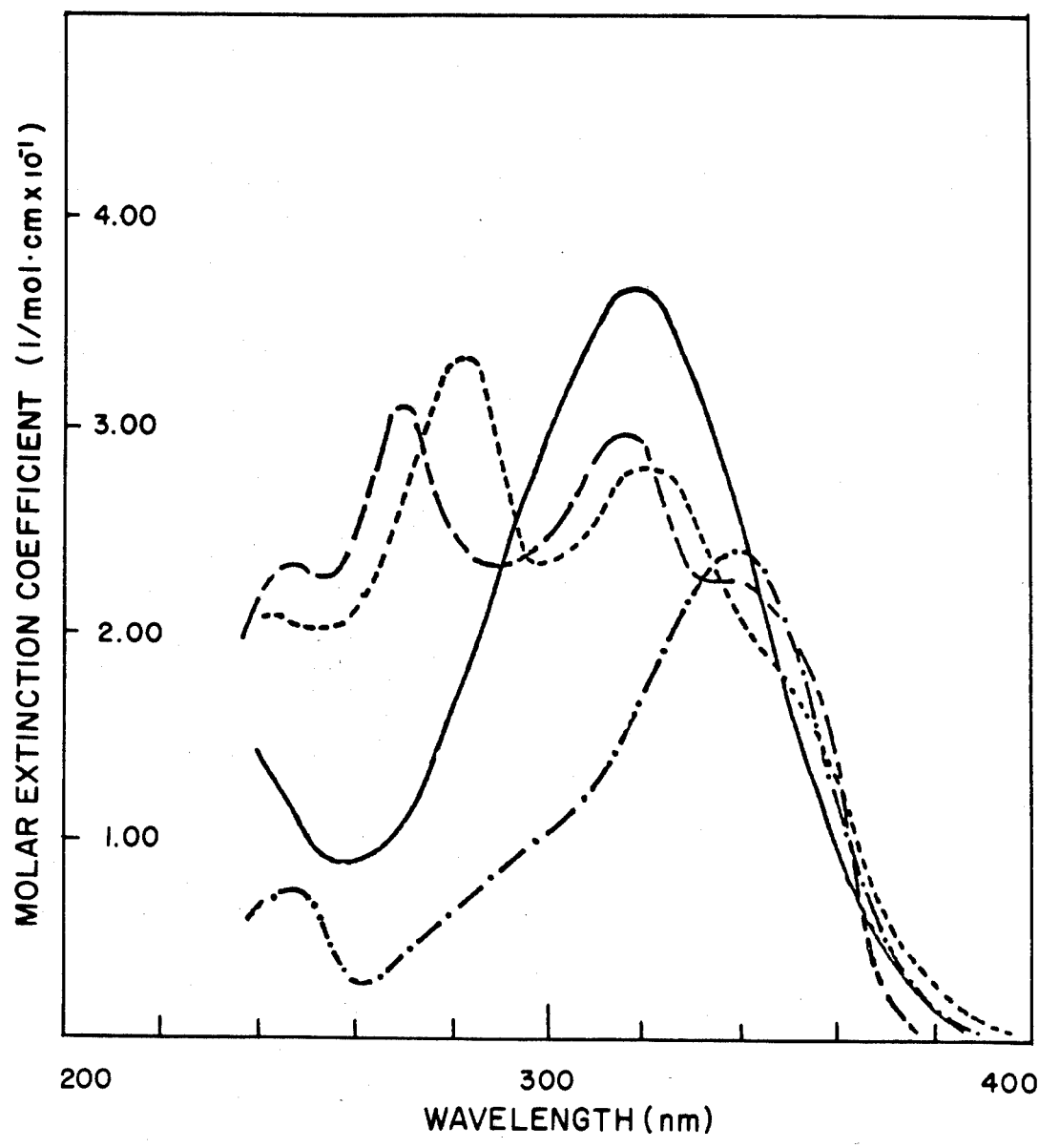

ULTRAVIOLET LIGHT ABSORBERS HAVING TWO DIFFERENT CHROMOPHORS IN THE SAME MOLECULE

This invention relates to novel ultraviolet light absorbers having two chromophors in the same molecule, and more particularly to benzotriazole substituted dihydroxybenzophenones and acetophenones. More particularly, this invention relates to 3,5-[di(2H-benzotriazole-2-yl)]-2,4-dihydroxybenzophenone and 3,5-[di(2H-benzotriazole-2-yl)]-2,4-dihydroxyacetophenone which are particularly useful as ultraviolet light absorbers.

BACKGROUND

Since the discovery of 2(2-hydroxyphenyl)2H-benzotriazoles as effective ultraviolet light absorbers and ultraviolet stabilizers, especially in plastic materials, much attention has been paid to the synthesis of novel and unusual 2(2-hydroxyphenyl)2H-benzotriazole derivatives.

More recently, attention has shifted to less volatile, more compatible and ultimately polymerizable, polymeric and polymer bound ultraviolet stabilizers of the 2(2-hydroxyphenyl)2H-benzotriazole (2HB) category. Initial photophysical studies showed these compounds to be effective ultraviolet stabilizers. There are also some indications that some of these compounds may also act as quenchers of the excited states.

Before the use of the 2(2-hydroxyphenyl)2H-benzotriazoles (2HB's), ultraviolet stabilizers of the category of 2-hydroxybenzophenones were, and still are, used extensively, but few polymerizable 2-hydroxybenzophenone ultraviolet stabilizers are now available commercially. Such compounds are typified in U.S. Pat. Nos. 2,938,883 to Raisch and 2,947,723 to Clark.

Although much synthetic work has been done on the synthesis of 2(2-hydroxyphenyl)2H-benzotriazole (2HB's) some years ago, no attempts were made to combine the 2(2-hydroxyphenyl)2H-benzotriazole and the 2-hydroxybenzophenone chromophor in one molecule. It has been found that more than one benzotriazole unit may be easily introduced in one molecule when highly activated. Multi-hydroxylated phenyl compounds such as resorcinol or phloroglucinol have been used to produce a new series of compounds with interesting ultraviolet absorbing properties.

OBJECTS OF THE INVENTION

A primary object of the present invention is to provide an ultraviolet absorbing compound having both the 2(2-hydroxyphenyl)2H-benzotriazole and the 2-hydroxybenzophenone or the 2-hydroxyacetophenone chromophors in a single molecule.

A further object of this invention is to provide new ultraviolet absorbers of the 3,5-[di(2H-benzotriazole)]-2,4-dihydroxybenzophenone or acetophenone type.

Another object of this invention is to provide 3,5-[di(2H-benzotriazole-2-yl)]-2,4-dihydroxybenzophenone as a new ultraviolet absorbing compound.

Yet another object of this invention is to provide 3,5-[di(2H-benzotriazole-2-yl)]-2,4-dihydroxyacetophenone as a new ultraviolet absorbing compound.

These and other objects and advantages of the present invention will become apparent when considered in light of the following description and claims.

SUMMARY OF THE INVENTION

The 3,5-[di(2H-benzotriazole-2-yl)]-2,4-dihydroxybenzophenone and 3,5-[di(2H-benzotriazole-2-yl)]-2,4-dihydroxyacetophenone of the present invention are prepared by the condensation of o-nitrobenzenediazonium chloride with 2,4-dihydroxybenzophenone and 2,4-dihydroxyacetophenone, respectively, followed by reductive ring closure with zinc dust and sodium hydroxide. The synthesis of these compounds makes ultraviolet absorbers available for the study of the photophysical behavior of compounds with two different chromophors.

The 3,5-[di(2H-benzotriazole-2-yl)]-2,4-dihydroxybenzophenone and 3,5-[di(2H-benzotriazole-2-yl)]-2,4-dihydroxyacetophenone compounds of the invention show infrared characteristics typical for their structure as seen in FIGS. 1 and 2 of the accompanying drawings.

The $^{13}$C NMR chemical shift data of 3,5-[di(2H-benzotriazole-2-yl)]-2,4-dihydroxybenzophenone and 3,5-[di(2H-benzotriazole-2-yl)]-2,4-dihydroxyacetophenone showed characteristic chemical shift values expected for such compounds. Good agreement of the experimental data was found with the calculated values, with the exception of the substituted carbon atom to which the hydroxyl group is attached but flanked with two benzotriazole groups. The $^{13}$C chemical shift data of the carbon atom "e" substituted with a hydrogen and the carbonyl carbon atom "g" (Tables I and II, and FIGS. 3 and 4) also show deviations from the calculated values.

The ultraviolet spectra of the 3,5-[di(2H-benzotriazole-2-yl)]-2,4-dihydroxybenzophenone (DBDB) and 3,5-[di(2H-benzotriazole-2-yl)]-2,4-dihydroxyacetophenone (DBDA) are shown in FIG. 5, with the numerical value of the spectra described in Tables III and IV. The compound (DBDA) has four maxima with $\lambda_{max}$ at 252 nm, 273 nm, 322 nm, and 343 nm with extinction coefficients from $23 \times 10^3$ to $31 \times 10^3$ L$\times$mol$^{-1}\times$cm$^{-1}$, while DBDB has $\lambda_{max}$ at 246 nm, 285 nm, and 327 nm, and extinction coefficients of $21.5 \times 10^3$, $35.1 \times 10^3$ and $29.3 \times 10^3$ L$\times$mol$^{-1}\times$cm$^{-1}$.

The absorption behavior of the compounds shows exceptionally broad absorption bands which range from about 250 nm to 360 nm.

DESCRIPTION OF THE PREFERRED EMBODIMENTS

Example 1

Preparation Of 3,5-[Di(2H-benzotriazole-2-yl)]-2,4-dihydroxyacetophenone

Figure 1:
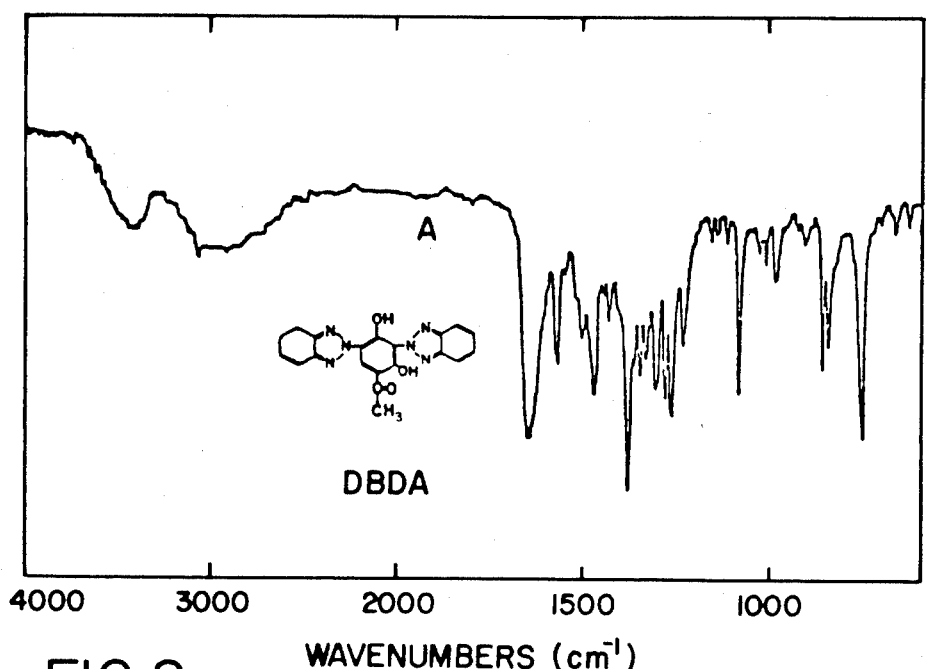
Figure 2:
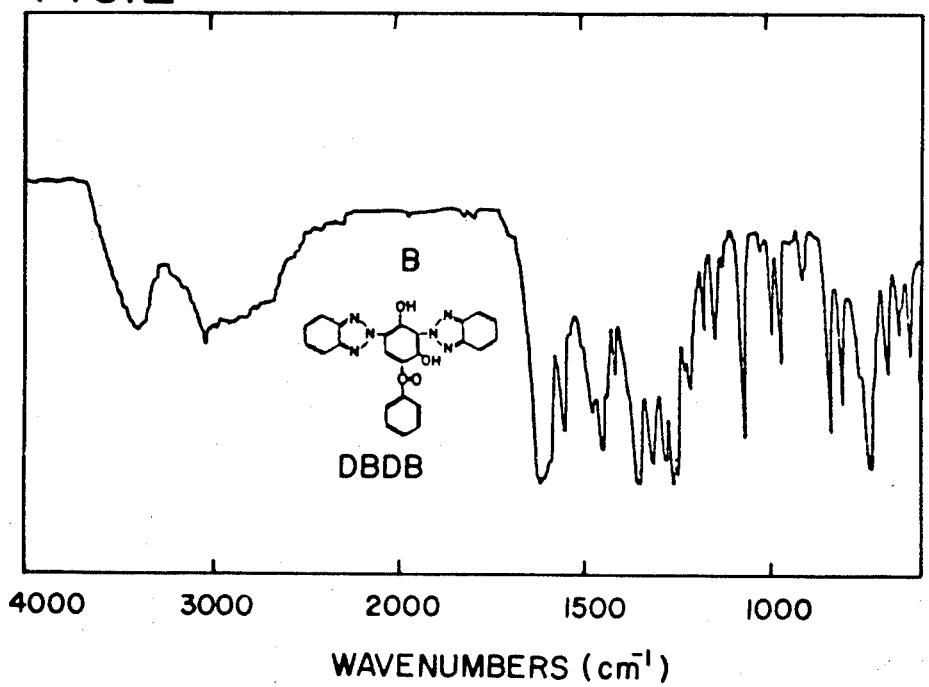
Figure 3:
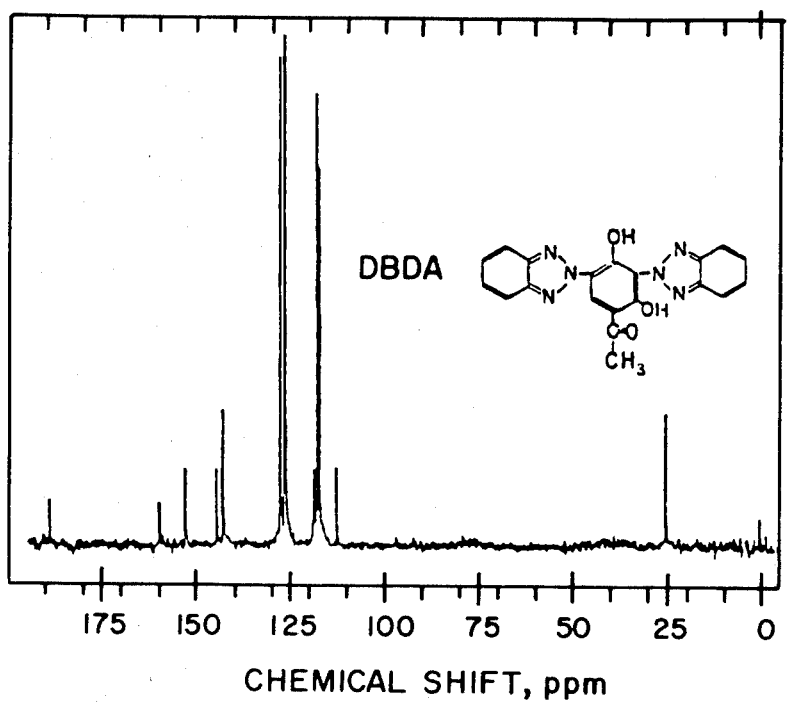
Figure 4:
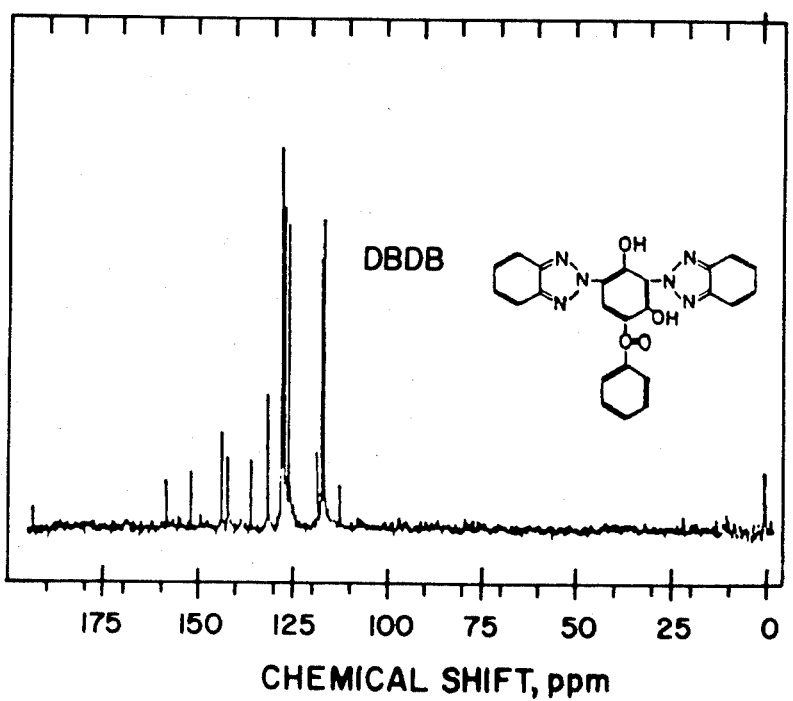

A solution of o-nitroaniline (55 g, 0.4 mol) in concentrated hydrochloric acid (150 ml) was diazotized with a solution of sodium nitrite (28 g, 0.4 mol) in water (100 ml) at 0° C., following known procedures. The cold solution of o-nitrobenzenediazonium chloride was added over a period of 1 hour with stirring to a solution of 2,4-dihydroxyacetophenone (30 g, 0.2 mol), sodium hydroxide (16 g, 0.4 mol), sodium carbonate (90 g, 0.72 mol) in water (900 ml) at 5°–10° C. The red azo compound was washed 3 times with water at about 60° C., then dissolved in 600 ml of aqueous 2N sodium hydroxide (1.2 mol) and was reductively ring closed at 50° C. in one hour with zinc dust (120 g, 1.84 mol), and additional 40% sodium hydroxide (150 ml) solution.

After one day at room temperature the suspension was filtered and the residue was extracted twice with 10% aqueous sodium hydroxide; the filtrate was combined with this extract and cooled in an ice bath. While keeping the temperature below 10° C., the solution was acidified with concentrated hydrochloric acid. Crude 3,5-[di(2H-benzotriazole-2-yl)]-2,4-dihydroxyacetophenone (DBDA) precipitated and was isolated by filtration, air dried and extracted for 3 days with benzene in a Soxhlet extractor. DBDA (25 g, 32% yield) was isolated from the benzene extract.

Recrystallization from chloroform and benzene 1:1 gave pure DBDA as pale yellow needles; m.p. 265°–267° C. The ultraviolet absorption data are shown in Table III. The infrared spectrum was obtained in KBr as: 3420 cm$^{-1}$ (O—H stretching).

The $^1$H NMR spectrum showed $\delta=2.7$ ppm (CH$_3$ 3H singlet), $\delta=7.2$–7.6 ppm and 7.7–8.1 ppm (protons of the benzotriazole group, 8H multiplet), $\delta=9.1$ ppm (6-proton of phenoxy group, 1H singlet), $\delta=11.7$ and 13.3 ppm (OH 2H, singlet). The $^{13}$NMR chemical shift data are shown in Table I.

The analysis calculated for C$_{20}$H$_{14}$N$_6$O$_3$ is C, 62.17%; H, 3.65%; N, 21.75%. The analysis found for the compound was C, 61.98%; H, 3.48%; N, 21.76%.

Example 2

Preparation of 3,5-[Di(2H-benzotriazole-2-yl)]-2,4-dihydroxybenzophenone

A solution of o-nitroaniline (55 g, 0.4 mol) in concentrated hydrochloric acid (150 ml) was diazotized with a solution of sodium nitrite (28 g, 0.4 mol) in water (100 ml) at 0° C., following known procedures. The cold solution of o-nitrobenzenediazonium chloride was added at a molar ratio of 2:1 to 2,4-dihydroxybenzophenone with sodium bicarbonate (118 g, 1.4 mol), sodium carbonate (110 g, 0.088 mol) in water (900 ml) at about 5°–10° C.

The red azo compound was then washed three times with water at about 60° C., dissolved in 600 ml of aqueous 2N sodium hydroxide (1.2 mol), and was reductively ring closed at 50° C. in about one hour with zinc dust (120 g, 1.84 mol), and additional 40% sodium hydroxide (150 ml) solution.

Crude 2,5-[di(2H-benzotriazolyl)]-1,3-dihydroxy-4-benzophenone was extracted for two days with ethanol in a Soxhlet apparatus, and the ethanol extract yielded 8 g (9% of 2,5-[di(2H-benzotriazolyl)]-1,3-dihydroxy-4-benzophenone. Recrystallization from chloroform/ethanol 3:1 gave yellow needles, m.p. 254°–255° C. The ultraviolet absorption data are presented in Table 2. Infrared (KBr) results: 3420 cm$^{-1}$ (O—H stretching).

The $^1$H NMR spectrum showed $\delta=7.2$–8.1 ppm (protons of benzotriazole group and phenyl ring, 13H broad), $\delta=9.1$ ppm (6-proton of phenoxy group, 1H singlet), $\delta=13.0$ and 13.3 ppm (OH, 2H singlet). $^{13}$C NMR chemical shift data are presented in Table 2.

The analysis calculated for C$_{25}$H$_{16}$N$_6$O$_3$ is: C, 66.96%; H, 3.60%; N, 18.74%.

The analysis found for the compound was C, 66.73%; H, 3.25%; N, 18.53%.

TABLE I $^{13}$C NMR Chemical Shift Data for 2H—Benzotriazole Substituted 3,5-[Di(2H—benzotriazole-2-yl)]-2,4-dihydroxyacetophenone

| Assignment | Chemical Shift | Obs. Int (a) | Obs. CS (b) | Calcltd. CS (b) |
|---|---|---|---|---|
| Phenoxy Group | a | 21 | 153.1 | 155.9 |
| | b | 12 | 118.7 | 119.5 |
| | c | 13 | 159.9 | 159.2 |
| | d | 22 | 113.1 | 113.4 |
| | e | 31 | 126.4 | 128.9 |
| | f | 21 | 119.1 | 120.9 |
| Benzotriazole Group | 1 (c) | 35 | 143.0 | 143.2 |
| | 2 (c) | 94 | 117.5 | 117.6 |
| | 3 (c) | 120 | 128.0 | 127.0 |
| | 4 (c) | 21 | 144.8 | 144.4 |
| | 5 (c) | 112 | 118.3 | 118.3 |
| | 6 (c) | 125 | 126.8 | 126.5 |
| Substituent Group | g | 8 | 189.2 | 202.3 |
| | h | 35 | 26.3 | 26.1 |
| | i | — | — | — |
| | j | — | — | — |
| | k | — | — | — |

(a) Int: Relative Intensity
(b) CS: Chemical Shift Values (ppm from internal TMS) samples in CDCl$_3$
(c) Tentative Assignments

TABLE II $^{13}$C NMR Chemical Shift Data for 2H—Benzotriazole Substituted 3,5-[Di(2H—Benzotriazole-2-yl)]-2,4-dihydroxybenzophenone

| Assignment | Chemical Shift | Obs. Int (a) | Obs. CS (b) | Calcltd. CS (b) |
|---|---|---|---|---|
| Phenoxy Group | a | 20 | 153.1 | 157.0 |
| | b | 10 | 119.5 | 120.3 |
| | c | 18 | 159.7 | 162.8 |
| | d | 17 | 113.8 | 112.8 |
| | e | 58 | 128.6 | 131.4 |
| | f | 28 | 119.7 | 121.1 |
| Benzotriazole Group | 1 (c) | 25 | 143.3 | 143.2 |
| | 2 (c) | 102 | 117.8 | 117.6 |
| | 3 (c) | 105 | 128.1 | 127.0 |
| | 4 (c) | 33 | 144.9 | 144.4 |
| | 5 (c) | 90 | 118.5 | 118.3 |
| | 6 (c) | 100 | 127.1 | 126.5 |
| Substituent Group | g | 12 | 194.0 | 199.4 |
| | h | 25 | 137.2 | 138.3 |
| | i | 125 | 128.8 | 128.2 |
| | j | 105 | 129.2 | 128.6 |

TABLE III

Ultraviolet Absorption of 3,5-[Di(2H—benzotriazole-2-yl)]-2,4-dihydroxyacetophenone

| $\lambda max$ | $\epsilon L \times mol^{-1} \times cm^{-1} \times 10^{-3}$ | $\lambda max$ | $\epsilon L \times mol^{-1} \times cm^{-1} \times 10^{-3}$ | $\lambda max$ | $\epsilon L \times mol^{-1} \times cm^{-1} \times 10^{-3}$ | $\lambda max$ | $\epsilon L \times mol^{-1} \times cm^{-1} \times 10^{-3}$ |
|---|---|---|---|---|---|---|---|
| 252 | 23.5 | 273 | 30.8 | 322 | 29.7 | 343 | 23.2 (shoulder) |

Absorptions determined in solutions of chloroform
Concentration: $2 \times 10^{-5}$ mol/L

TABLE IV

Ultraviolet Absorption of 3,5-[Di(2H—benzotriazole-2-yl)]-2,4-dihydroxybenzophenone

| $\lambda max$ | $\epsilon L \times mol^{-1} \times cm^{-1} \times 10^{-3}$ | $\lambda max$ | $\epsilon L \times mol^{-1} \times cm^{-1} \times 10^{-3}$ | $\lambda max$ | $\epsilon L \times mol^{-1} \times cm^{-1} \times 10^{-3}$ |
|---|---|---|---|---|---|
| 246 | 21.5 | 285 | 35.1 | 327 | 29.3 |

Absorptions determined in solutions of chloroform
Concentration: $2 \times 10^{-5}$ mol/L

TABLE II-continued

13C NMR Chemical Shift Data for 2H—Benzotriazole Substituted 3,5-[Di(2H—Benzotriazole-2-yl)]-2,4-dihydroxybenzophenone Compound

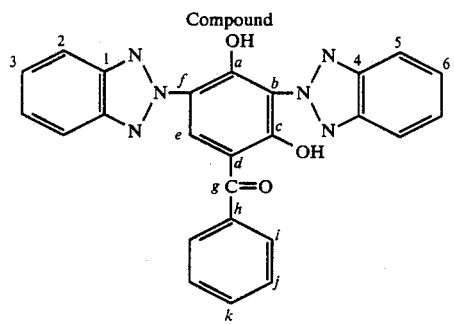

| Assignment | Chemical Shift | Obs. Int (a) | Obs. CS (b) | Calcltd. CS (b) |
|---|---|---|---|---|
| k | | 45 | 132.8 | 131.2 |

(a) Int: Relative Intensity
(b) CS: Chemical Shift Values (ppm from internal TMS) samples in CDCl₃
(c) Tentative Assignments

We claim:
1. 3,5-[Di(2H-benzotriazole-2-yl)]-2,4-dihydroxyacetophenone.
2. An ultraviolet light absorbing compound having the structural formula

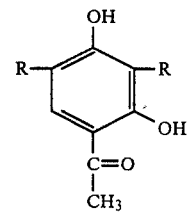

wherein R is a benzotriazole group.